United States Patent
Crespo

(10) Patent No.: US 7,400,258 B2
(45) Date of Patent: Jul. 15, 2008

(54) SUBSTANCE TESTING DEVICES WITH PHOTO IDENTIFICATION

(75) Inventor: Pierre M. Crespo, Zelienople, PA (US)

(73) Assignee: Biometric Equipment & Safety Technology Labs, Inc., Harrisburg, PA (US)

( * ) Notice: Subject to any disclaimer, the term of this patent is extended or adjusted under 35 U.S.C. 154(b) by 234 days.

(21) Appl. No.: 11/252,969

(22) Filed: Oct. 17, 2005

(65) Prior Publication Data

US 2006/0097881 A1    May 11, 2006

Related U.S. Application Data

(63) Continuation of application No. 10/026,728, filed on Dec. 21, 2001, now Pat. No. 6,956,484.

(51) Int. Cl.
*G08B 23/00* (2006.01)

(52) U.S. Cl. .................. 340/573.1; 348/156
(58) Field of Classification Search ............. 340/573.1, 340/576, 426.11; 73/23.3; 348/156
See application file for complete search history.

(56) References Cited

U.S. PATENT DOCUMENTS

| | | | | |
|---|---|---|---|---|
| 3,780,378 | A * | 12/1973 | Simonson | 396/332 |
| 6,205,840 | B1 * | 3/2001 | Thompson | 73/23.3 |
| 2002/0031752 | A1 * | 3/2002 | Kouba et al. | 434/219 |

FOREIGN PATENT DOCUMENTS

GB    2126394 A  *  3/1984

* cited by examiner

*Primary Examiner*—Thomas Mullen
(74) *Attorney, Agent, or Firm*—Ference & Associates LLC

(57) ABSTRACT

A system which, in at least one embodiment, obtains a photographic image of an individual attempting to disengage an ignition interlock device or the like to assist in determining whether the individual is the same as one for whom the device is intended.

34 Claims, 2 Drawing Sheets

SUBSTANCE TESTING DEVICES WITH PHOTO IDENTIFICATION

CROSS REFERENCE TO RELATED APPLICATIONS

This application is a continuation of prior U.S. patent application Ser. No. 10/026,728, filed Dec. 21, 2001, now U.S. Pat. No. 6,956,484, which is hereby incorporated by reference in its entirety as if fully set forth herein.

FIELD OF THE INVENTION

The present invention relates generally to ignition interlock devices, such as are used in vehicles of drivers with DUI convictions (who, e.g., are endowed with special driving privileges and are in that connection under supervision by a probation officer or the state as a condition of such privileges).

BACKGROUND OF THE INVENTION

Essentially, an ignition interlock is a device that includes a breathalyzer which prohibits a vehicle from starting if the breathalyzer returns a reading of "under the influence" (i.e., corresponding to a statutory level of impairment or even a lower level of impairment prescribed by the manufacturer). Several courts throughout the U.S. are now requiring that interlock devices be placed in vehicles operated by individuals convicted of DUI offenses. The "LIFESAFER"™ ignition interlock system of the LifeSafer Interlock company (Cincinnati, Ohio) is a well-known conventional example. In it, a buzz tone is emitted during a breathalyzer test to indicate when a deep breath sample containing alveolar air has been provided and, thus, is sufficient to be analyzed.

It has been found that a major drawback of conventional interlock devices is that they might not be effective in deterring DUI offenses if an individual other than the defendant (i.e., the person who has been assigned the interlock device) actually operates the interlock. For instance, a defendant who is once again "under the influence" still might be able to operate the vehicle by asking his/her friend or spouse to supply a "clean" breath sample that will unlock the ignition.

A general solution that has been sought to eradicate this "loophole" has been to require an original "breath pattern" from the defendant against which subsequent attempts to unlock the ignition are compared; this helps thwart the occurrence of non-genuine breath samples. Examples of such an arrangement is disclosed in U.S. Pat. Nos. 4,738,333, 4,912,458 and 4,901,058. However, this solution has been found to present numerous difficulties and drawbacks. For instance, accuracy in comparing "breath patterns" can be highly elusive.

U.S. Pat. No. 6,229,908 discloses an ignition interlock system in which an individual's fingerprint may be used to verify his/her identity and blood-alcohol content is determined using spectroscopic analysis of the finger from which the fingerprint is obtained. Aside from cost considerations, a major drawback to such a device is that for purposes of motor vehicle operation, state statutes specify the manner in which blood-alcohol content is to be determined and spectroscopic analysis is generally not so specified. Rather, the use of a breathalyzer is typically called for. It would not be sufficient to use fingerprint authentication for interlock devices, because as discussed above, the defendant may provide the authentication while someone else supplies a "clean" breath.

A need has therefore been recognized in connection with providing an effective, foolproof ignition interlock device that precludes loopholes of the type described above.

SUMMARY OF THE INVENTION

In accordance with at least one presently preferred embodiment of the present invention, it is contemplated that a system be provided that obtains a photographic image of an individual attempting to disengage an ignition interlock device. Preferably, the photographic image is obtained simultaneously with a breath being blown into the breathalyzer device. Response of the breathalyzer device may preferably be recorded by time and date along with the obtained image. On a periodic basis, photographed images can then be reviewed during routine maintenance, in order to adequately ascertain whether the operator of the vehicle (or other machinery) in each instance indeed corresponded to the individual for whom the interlock device was intended.

In summary, the present invention provides, in one aspect, an apparatus for identifying one or more individuals impaired by a controlled substance, the apparatus comprising: a detection device being adapted to ascertain the degree to which an individual is affected by a controlled substance; and a photographic unit; the photographic unit being operable, responsive to the detection device, to facilitate photographic identification of an individual tested by the detection device who is affected by a controlled substance beyond a predetermined threshold level.

In another aspect, the present invention provides a method of identifying one or more individuals impaired by a controlled substance, the method comprising the steps of: providing a photographic unit; ascertaining the degree to which an individual is affected by a controlled substance; and operating the photographic unit, responsive to the ascertaining step, to facilitate photographic identification of an individual who is affected by a controlled substance beyond a predetermined threshold level.

For a better understanding of the present invention, together with other and further features and advantages thereof, reference is made to the following description, taken in conjunction with the accompanying drawings, and the scope of the invention will be pointed out in the appended claims.

DESCRIPTION OF THE PREFERRED EMBODIMENTS

Figure 1:
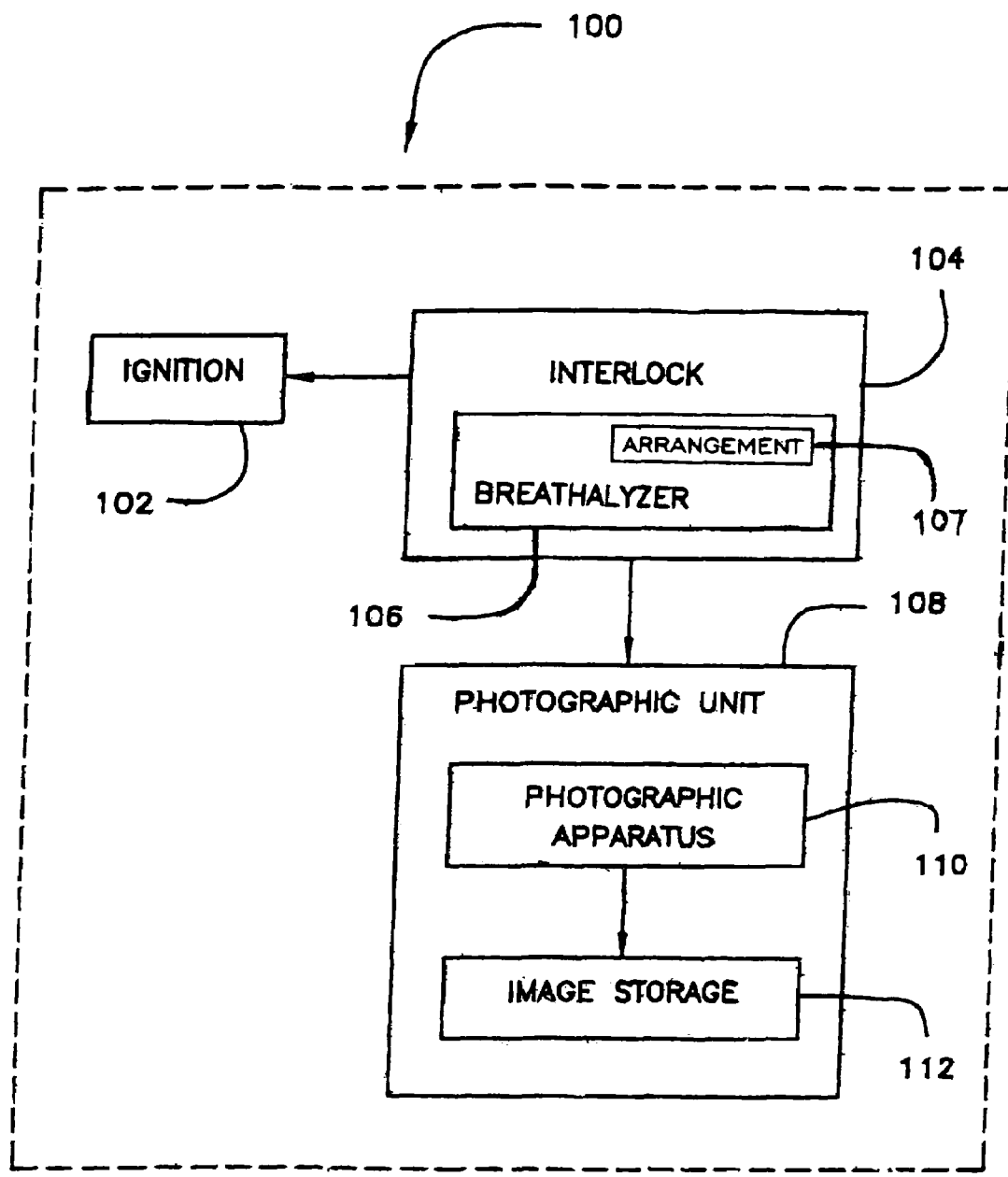
FIG. 1 schematically illustrates an ignition interlock device with photo identification.

FIG. 1 schematically illustrates a motor vehicle 100 or other machinery in which an ignition interlock device, in accordance with at least one embodiment of the present invention, may be employed.

An ignition 102 of the vehicle 100 (or other machinery) may be engageable via interlock device 104. Interlock device 104 preferably includes a breathalyzer 106. A photographic unit 108, on the other hand, preferably includes a photographic apparatus 110 and image storage arrangement 112.

Preferably, an individual (who is likely a defendant required to use an ignition interlock device), when wishing to start the ignition 102, will take a test with breathalyzer 106 in conventional manner (e.g. via emitting a sufficient blow of his/her breath into the equipment). If the test determines a state of "under the influence" then, per usual, the interlock device 104 will engage to prevent activation of ignition 102 and, thus, operation of the vehicle 100 or other machinery. Preferably, breathalyzer 106 will also include an arrangement 107 (as conventionally known) for determining whether a breath sample provided by the operator is suitable for testing in the first place. As discussed below, this arrangement 107 will preferably serve to provide an activation prompt to photographic unit 108. Thus, in accordance with a preferred embodiment of the present invention, the activation of photographic unit 108 will immediately prompt photographic apparatus 110 to take a picture of the individual who is in the process of taking a breathalyzer test. Thus, the photographic apparatus 110 will preferably be mounted in such a manner as to obtain a good view of an individual in the position at which the breathalyzer test is being taken (e.g. it could be mounted inside an automobile and aimed towards the driver's seat). The image storage arrangement 112, preferably integral with the photographic apparatus 110, will preferably be suitable for storing the obtained photographic image until such a time that it and other stored images are reviewed to determine whether the image of the photographed individual corresponds to the individual for whom the ignition interlock device is intended. In other words, for example, photographed images (preferably those corresponding to a "failure" condition, or an impaired state of one or more individuals) can be reviewed on a periodic basis during routine maintenance, in order to adequately ascertain whether the operator of the vehicle (or other machinery) in each instance indeed corresponded to the individual for whom the interlock device was intended. Conceivably, when a "failure" state is indicated for a particular incident, a court may be notified. It should well be appreciated that by having an image of an individual who was being tested at the time of a "failure", a court would have the ability to confidently enforce violations of probation orders (e.g., by preventing a defendant from asserting that someone else was being tested at that point in time).

As discussed above, interlock device 104 will preferably provide a prompt in order for photographic unit 108 to be activated. Although such a prompt may take any of a large number of conceivable forms, it is presently contemplated in accordance with an embodiment of the present invention that the prompt be an audible prompt (wherein the photographic unit 108 would include an appropriate audio receptor, not shown, that is suitable for detecting the audible prompt and thence activating the photographic apparatus 110). In a further refinement, such an audible prompt could be similar to the buzz tone associated with the aforementioned "LIFE-SAFER"™ interlock device, whereby the buzz tone would serve to activate the photographic unit 108.

In accordance with a preferred embodiment of the present invention, the photographic apparatus 110 and image storage arrangement 112 are integrated into a single, cohesive unit (e.g. in a common housing). The "SILENT WITNESS"™ camera manufactured by Silent Witness Enterprises Ltd., Surrey, British Columbia, Canada, represents a highly favorable arrangement that could function as just described, that is, which includes both a camera and an image storage arrangement.

Although in a presently preferred embodiment of the present invention it is contemplated that an ignition interlock device be employed in an automobile or other motor vehicle, it is conceivable to employ the interlock device in other settings. For instance, the machinery 100 illustrated in FIG. 1 could be in the form of machinery at a factory or plant (e.g. a printing press, lathe machinery, etc.) that would only be operable upon a worker taking a breathalyzer test and being positively identified via a photographic apparatus, in a manner similar to that discussed heretofore.

Several advantages are apparent in connection with an ignition interlock device in accordance with at least one embodiment of the present invention. Employers may find such a device highly desirable as it may accord protection from liability in situations where there might otherwise be an accident as a result of a worker who is intoxicated (or otherwise affected by a controlled substance beyond a predetermined threshold level) on the job. Settings where this may be useful could include, for example, public transportation companies (where, for instance, bus or trolley drivers would undergo the breathalyzer test prior to operating a vehicle), trucking companies, and even in manufacturing environments, as described above, in which heavy or complex machinery is operated and in which significant dangers are presented if an operator is otherwise intoxicated (or otherwise affected by a controlled substance beyond a predetermined threshold level).

Another potential employment setting would be a timeclock apparatus. In this scenario, photographic images would be obtained of employees, "punching in" to a timeclock, who are impaired by a controlled substance. Any employee so impaired would thus be deterred from having another individual punch the timeclock in his/her place. Such an embodiment would appear to be appropriate in instances, e.g., in which an employer may wish to bar an employee, who is impaired by a given controlled substance beyond a given threshold level, from working that day (or after lunch, when an employee may have had access to alcohol), regardless of whether or not the employee is to operate machinery.

Figure 2:
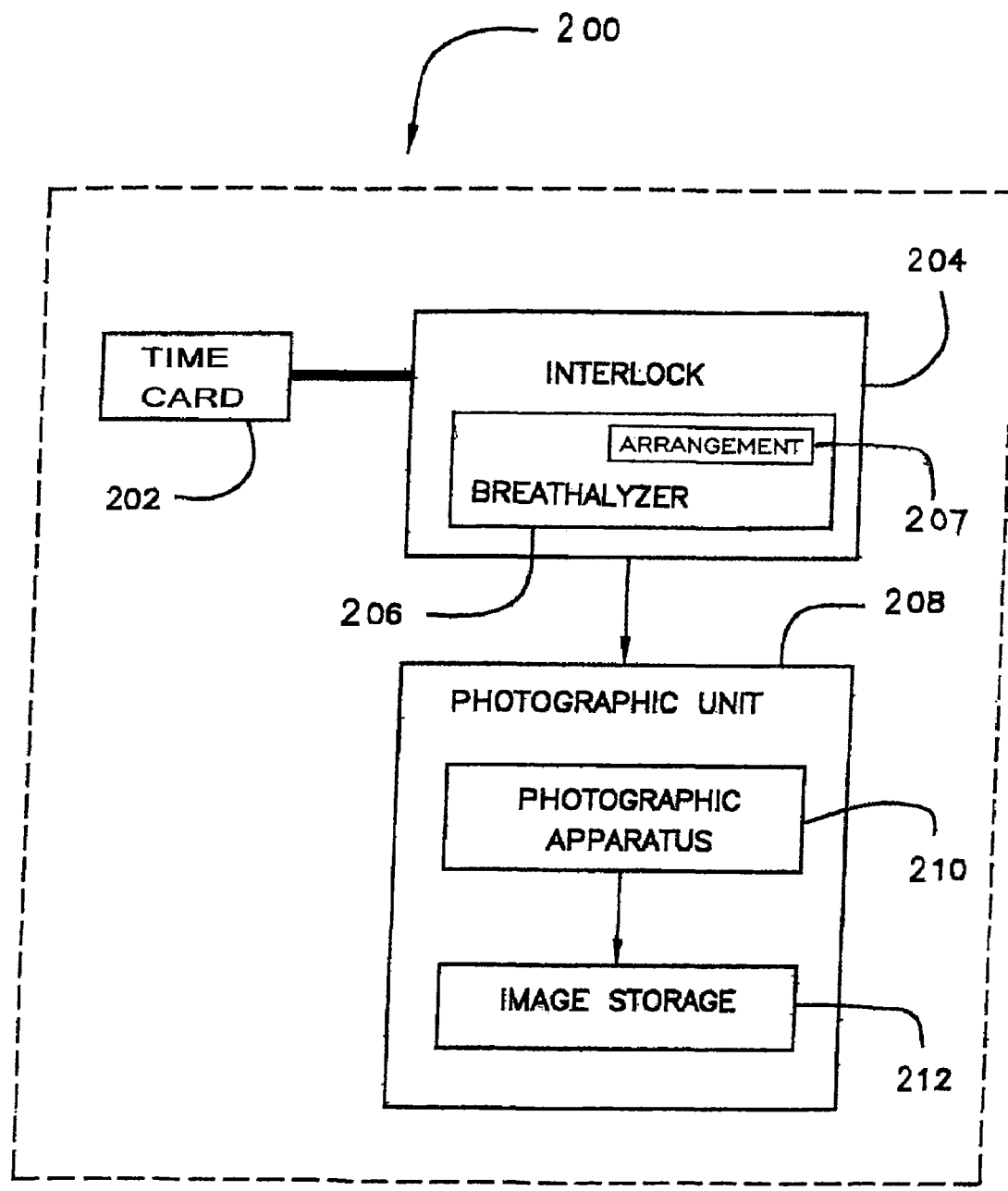
FIG. 2 schematically illustrates a timeclock apparatus with photo identification.

FIG. 2 schematically illustrates a timeclock apparatus 200 in which an interlock device, in accordance with at least one embodiment of the present invention, may be employed. A timeclock apparatus 200 with time card slot 202 may be engageable via interlock device 204. Interlock device 204 preferably includes a breathalyzer 206. A photographic unit 208, on the other hand, preferably includes a photographic apparatus 210 and image storage arrangement 212.

It is believed that the inclusion of a photographic apparatus in an ignition interlock device in a motor vehicle or other machinery will provide an additional deterrence factor that may help reduce the likelihood of drunk driving (or impaired machine operation) even further. Particularly, the mere presence of the photographic apparatus, through profound psychological effect, may well provide a significant impetus for an individual to avoid even contemplating any type of loophole for circumventing the interlock.

Although the use of photographic apparatus and image identification has been utilized in "home arrest" settings, it is believed that the presently contemplated use of photographic apparatus and positive identification in connection with the operation of motor vehicles or other machinery has never been contemplated. In a "home arrest" setting, an individual who is confined to the home for part or all of the day and who wears a tracking device, such as an ankle bracelet, to deter unwarranted flight, may be required to "check in" at a breathalyzer device in the home at predetermined times, or even at random times, throughout the day in order to impart a standard of behavior modification. Among many other possibilities, a visual image of the individual may then be transmitted over a communications link to present a visual image of the prisoner, e.g., at a police station or monitoring service. However, the "home arrest" arrangement just described does not serve to prevent or allow the operation of machinery. (An example of such a "home arrest" arrangement may be found in U.S. Pat. No. 4,843,377.)

Though the disclosure heretofore has largely focused on contexts in which alcohol consumption is consumed, it should be understood that the embodiments of the present invention are applicable to other types of controlled substances as well, such as, for example, a narcotic drug (e.g., cocaine, heroin or marijuana). In such cases, appropriate detection equipment would be interfaced with an interlock in a vehicle or other machinery and could preferably operate in substantially similar manner as the inventive equipment described heretofore in connection with alcohol.

Though the disclosure heretofore has largely contemplated the use of photographic apparatus to record "still" shots of an individual, such as a digital camera that takes "snapshots", it should be understood that essentially any type of photographic equipment, configured for producing essentially any type of still or moving record of an individual, could be used, such as a VHS camera or camcorder.

If not otherwise stated herein, it is to be assumed that all patents, patent applications, patent publications and other publications (including web-based publications) mentioned and cited herein are hereby fully incorporated by reference herein as if set forth in their entirety herein.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. An apparatus for use in conjunction with a time-clocking apparatus for identifying one or more individuals impaired by a controlled substance, said apparatus comprising:
   a detection device being adapted to ascertain the degree to which said individual is affected by a controlled substance while the individual is punching a time card into said time-clocking apparatus;
   a photographic unit;
   said photographic unit being operable, responsive to said detection device, to facilitate photographic identification of an individual tested by said detection device who is affected by a controlled substance beyond a predetermined threshold level.

2. The apparatus according to claim 1, further comprising:
   an interlock device associated with said detection device, said interlock device being adapted to bar an individual from entering an area beyond said time clocking apparatus if a test conducted with said detection device indicates that the individual is affected by a controlled substance beyond a predetermined threshold level.

3. The apparatus according to claim 2, whereby the entrance of said individual into said individual's work place is enabled solely upon said interlock device being disengaged via a test conducted with said detection device indicating that an individual is not affected by a controlled substance beyond a predetermined threshold level.

4. The apparatus according to claim 2, wherein:
   said interlock device comprises means for providing a prompt;
   said photographic unit being operable upon a prompt being provided by said interlock device.

5. The apparatus according to claim 2, wherein said photographic unit comprises a photographic apparatus and means for storing photographic images.

6. The apparatus according to claim 5, wherein said photographic apparatus and said means for storing photographic images are combined in a single, integral device.

7. The apparatus according to claim 6, wherein said means for storing photographic images is adapted to facilitate the provision of at least one photographic image at a subsequent time in connection with ascertaining the identity of an individual tested via said detection device.

8. The apparatus according to claim 6, wherein said photographic apparatus and said detection device are combined in a single, integral device.

9. The apparatus according to claim 2, wherein the controlled substance is alcohol.

10. The apparatus according to claim 9, wherein said detection device comprises a breathalyzer device.

11. The apparatus according to claim 10, wherein:
    said interlock device comprises means for providing a prompt;
    said photographic unit being operable upon a prompt being provided by said interlock device.

12. The apparatus according to claim 11, wherein the prompt is an audible tone.

13. The apparatus according to claim 12, wherein the audible tone is a buzz tone.

14. The apparatus according to claim 11, wherein the prompt is responsive to the provision of a breath sample suitable for analysis by said breathalyzer device.

15. The apparatus according to claim 2, wherein the controlled substance is a narcotic drug.

16. The apparatus according to claim 2 wherein said photographic unit comprises a digital camera.

17. The apparatus according to claim 2, wherein said photographic unit Comprises a video recorder.

18. The apparatus according to claim 2, wherein said photographic unit and said detection device are combined in a single, integral device.

19. A method of identifying one or more individuals impaired by a controlled substance in conjunction with said individuals punching time cards into a time clocking apparatus, said method comprising the steps of:
    providing a photographic unit;
    ascertaining the degree to which an individual is affected by a controlled substance while said individual is punching said time card into said time clocking apparatus; and
    operating the photographic unit, responsive to said ascertaining step, to facilitate photographic identification of an individual who is affected by a controlled substance beyond a predetermined threshold level.

20. The method according to claim 19, further comprising the steps of:
    preventing the entry of said individual into an area beyond the time clocking apparatus if said ascertaining step yields that the individual is affected by a controlled substance beyond a predetermined threshold level.

21. The method according to claim 20, wherein:
    said ascertaining step comprises automatically providing a prompt;
    said operating step comprises operating the photographic unit upon the prompt being provided.

22. The method according to claim 20, wherein said step of providing a photographic unit comprises providing a photographic apparatus and providing means for storing photographic images.

23. The method according to claim 22, further comprising the step of facilitating, with the means for storing photographic images, the provision of at least one photographic image at a subsequent time in connection with ascertaining the identity of an individual tested in said ascertaining step.

24. The method according to claim 20, wherein the controlled substance is alcohol.

25. The method according to claim 24, wherein said ascertaining step comprises using a breathalyzer device to ascertain the degree to which an individual is affected by alcohol.

26. The method according to claim 25, wherein:
said ascertaining step comprises automatically providing a prompt; and
said operating step comprises operating the photographic unit upon the prompt being provided.

27. The method according to claim 26, wherein the prompt is an audible tone.

28. The method according to claim 27, wherein the audible tone is a buzz tone.

29. The method according to claim 26, wherein the prompt is responsive to the provision of a breath sample suitable for analysis by the breathalyzer device.

30. The method according to claim 26, wherein said photographic unit and said detection device are combined in a single, integral device.

31. The method according to claim 19, wherein the controlled substance is a narcotic drug.

32. The method according to claim 19, wherein the photographic unit comprises a digital camera.

33. The method according to claim 19, wherein the photographic unit comprises a video recorder.

34. The method according to claim 19, wherein said photographic unit and said detection device are combined in a single, integral device.

* * * * *